United States Patent [19]

Casella et al.

[11] Plant 4,406

[45] Apr. 10, 1979

[54] PEACH TREE

[75] Inventors: Samuel J. Casella, Swedesboro, N.J.; Earl E. Slaybaugh, Towson, Md.

[73] Assignee: Casella Bros. Sons Inc., Swedesboro, N.J.

[21] Appl. No.: 912,045

[22] Filed: Jun. 2, 1978

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Frank B. Robb

[57] ABSTRACT

There is disclosed a peach tree which is the result of budding from a limb sport discovered on the variety known as "M. A. Blake" (N.J. 117) characterized by its more vigorous tree habit with tough, non-brittle branches, attractive color and appearance of the fruit, substantially earlier fruit ripening than "M. A. Blake" and virtual immunity from canker and brown rot.

2 Drawing Figures

The present invention relates to a new and distinct variety of peach tree, designated by us as "Caselaqueen", which produces fruit of the yellow-fleshed, freestone type, the fruit having been initially noticed by us growing on a limb sport of the variety known as "M. A. Blake" (N.J. 117), an unpatented variety.

Our discovery was made in an orchard on cultivated property of Casella Bros. Sons, Inc., at Swedesboro, Gloucester County, N.J., where our attention was directed and attracted in the course of caring for and inspecting an orchard of "M. A. Blake" peach trees.

The single limb sport was particularly notable because the fruit ripened about ten days earlier than other fruit on the same and adjacent "M. A. Blake" trees in the area.

We therefore jointly took steps to carefully preserve the original tree on which the sport limb was discovered, keep it under close observation and to bud the same to other trees to determine its continuing production of fruit with the same characteristics.

Reproduction by budding was performed at Aspers, Adams County, Pa., where we have continued to observe and produce fruit on trees developed as a result of such budding and find that it embodies the desirable characteristics noted and such characteristics come true to form.

We have continued our observation of the original tree sport, and the progeny thereof derived as before noted, finding that the early ripening habit of our new variety continues, together with other desirable aspects, representing a unique combination of characteristics which distinguish the same from "M. A. Blake" and from all other peach varieties of which we are aware, as evidenced by the following features which are outstanding in the new sport:

(1) A tree size and shape having similarity to "M. A. Blake" but sometimes a little larger in size;

(2) A very vigorous tree habit, with tough branches that are not brittle;

(3) A fruit having a more attractive color and appearance than "M. A. Blake" though having some resemblance thereto;

(4) Hardiness to produce regular crops when spring frosts and cold temperatures reduce crops of "M. A. Blake";

(5) An earlier fruit ripening habit, averaging about ten days earlier, than the fruit of "M. A. Blake";

(6) Excellent resistance to canker and brown rot.

The accompanying drawing shows typical specimens of the fruit of our new variety, with the fruit being illustrated in opposite side elevation as well as base and stem end uppermost, and in transverse and vertical cross-section, all as depicted in color as nearly true as it is reasonably possible to make the same in a color illustration of this character.

There follows a detailed description of our new peach variety, with color terminology in accordance with Nickerson's Color Fan, published by Munsell Color Co. of Baltimore, Md., except where general color terms of ordinary dictionary significance are applicable:

Parentage: A limb sport on an "M. A. Blake" tree (unpatented).

Locality where grown and observed: Near Aspers, Adams County, Pa.

Dates of first and last pickings: About August 10 and August 15, respectively.

Tree: Large size; vigorous, spreading; open; hardy (produces regular crops when spring frosts or cold temperatures reduces crops of "M. A. Blake" to less than 25% in the same area); very productive; regular bearer.

*Trunk.*—Stocky; medium shagginess.

*Branches.*—Stocky; medium shagginess; dull. Color — Light olive brown. 2.5y 5/5. Lenticels — Numerous; large size.

*Leaves.*—Large; lanceolate; medium thickness; smooth. Length — About 7 to 7½ inches. Width — About 1¼ inches. Color — Dark yellowish green. 10 GY 4/5. Margin — Finely serrate. Petiole — Medium length; medium thickness. Glands — 3 to 4, alternate; small; reniform; green. Stipules — None.

Flower buds: Hardy; large size; medium length; plump; appressed; pubescent.

Flowers:

*Dates of first and full bloom.*—Usually 2 or 3 days before "M. A. Blake", but ranges from about March 18 to about April 8, with from about 3 to 5 days between first and full bloom, depending on weather conditions; early in comparison with other varieties.

*Size.*—Large. (about the size of the flowers of "M. A. Blake").

*Color.*—Strong pink. 10 RP 7/8.

Fruit:

*Maturity when described.*—Hard under-ripe (10 days before "M. A. Blake".)

*Size.*—Uniform. Axial diameter — about 2½ inches. Transverse diameter in suture plans — about 2½ inches. Diameter at right angles to suture plant — about 2½ inches.

*Form.*—Uniform symmetrical; globose.

*Suture.*—Distinct; shallow depth; extends from base to beyond, but discontinuous at apex.

*Ventral surface.*—Slightly lipped, with lips equal.

*Cavity.*—Flaring; elongated in suture plane, with suture showing on one side. Depth — about ½ inch. Breadth — about ½ inch. Markings — similar to "M. A. Blake".

*Base.*—Rounded.

*Apex.*—Short.

*Stem.*—Stout; glabrous; medium adherence to stone. Length — about ½ inch.

*Skin.*—Medium thickness; tough; free from flesh; no tendency to crack in wet or dry seasons. Color — Vivid red 5 R 5/13. Down — scant; short; does not roll up when rubbed.

*Flesh.*—Color — Moderate orange yellow. 7.5 Yr 8/8.

*Surface of pit cavity.*—Color — Red, with pink fibres.

*Amygadlin.*—Scant.

*Juice.*—Moderate quantity.

*Texture.*—Firm; fine; meaty; melting.

*Fibres.*—Few; fine; tender;

*Ripens.*—Evenly on both lips.

*Flavor.*—Acid; better than "M. A. Blake."

*Aroma.*—Pronounced.

*Eating quality.*—Good.

Stone: Free, parts from flesh smoothly.

*Size.*—Medium. Length — about 1½ inches. Breadth — about 1⅛ inches. Thickness — about ¾ inch.

*Form.*—Oval; cuneate toward base.

*Base.*—Oblique.

*Hilum.*—Broad; oval.

*Apex.*—Acute.

*Sides.*—Equal.

*Surfaces.*—Irregularly furrowed throughout; ridged throughout.

*Ridges.*—Rounded.

*Pits.*—Circular; elongated.

*Ventral edge.*—Thick; without wing throughout.

*Dorsal edge.*—Shallow broad grooves throughout; ridges on either side interrupted.

*Color.*—Strong red. 10 RP 4/12.

*Tendency to split.*—Has never shown any splitting in wet or dry seasons.

Disease resistance: No indications of canker and no susceptibility to brown rot, as determined by comparison with other varieties grown under the same conditions near Aspers, Pa., and when adjacent trees of "M. A. Blake" clearly showed the presence of canker.

Use: Dessert; culinary; canning.

Keeping quality: Good.

Shipping quality: Good.

We claim:

1. A new and distinct variety of peach tree producing fruit of the yellow-fleshed, freestone type, substantially as herein shown and described, characterized particularly as to novelty by the unique combination of a tree size and shape similar to "M. A. Blake" but a little larger in size, a very vigorous tree habit with tough branches that are not brittle, a fruit having a more attractive color, appearance and of larger size than that of "M. A. Blake" although having a general resemblance thereto, hardiness to produce regular crops when spring frosts and cold reduces crops of other varieties, an earlier fruit ripening habit, averaging about ten days earlier than "M. A. Blake", and excellent resistance to canker and brown rot.

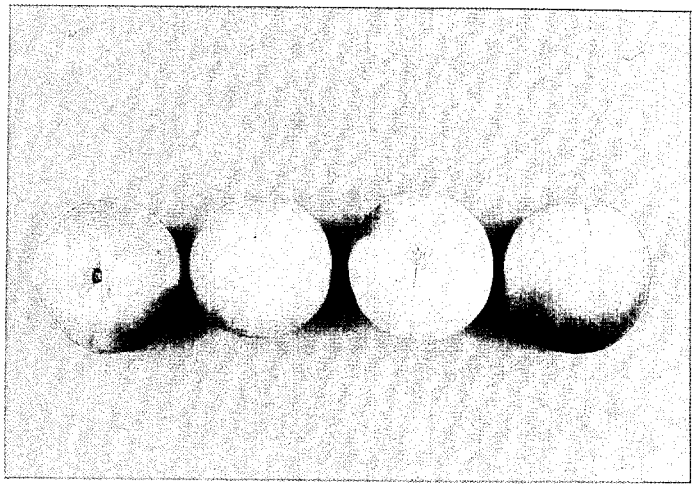
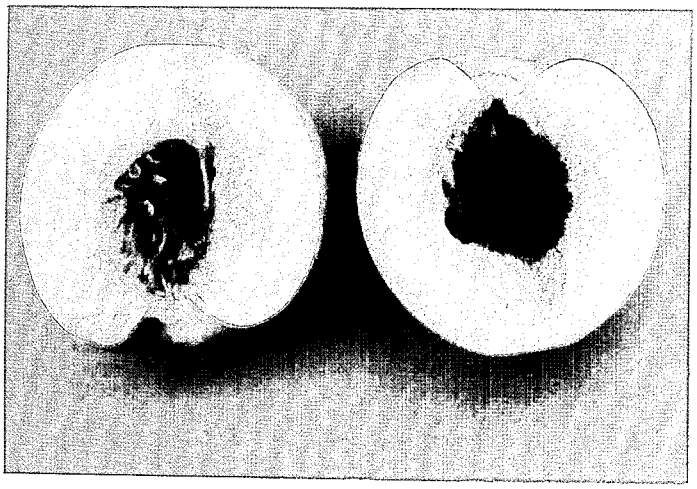

* * * * *